(12) United States Patent
Buckland et al.

(10) Patent No.: US 9,387,277 B2
(45) Date of Patent: Jul. 12, 2016

(54) BIOMEDICAL FILLER

(75) Inventors: Thomas Buckland, Cheddington (GB); Jonathan Arcos, St. Albans (GB)

(73) Assignee: ApaTech Limited, Elstree, Hertfordshire (GB)

( * ) Notice: Subject to any disclaimer, the term of this patent is extended or adjusted under 35 U.S.C. 154(b) by 1215 days.

(21) Appl. No.: 12/293,243

(22) PCT Filed: Mar. 19, 2007

(86) PCT No.: PCT/GB2007/000960
§ 371 (c)(1),
(2), (4) Date: Jun. 29, 2009

(87) PCT Pub. No.: WO2007/107729
PCT Pub. Date: Sep. 27, 2007

(65) Prior Publication Data
US 2009/0306789 A1    Dec. 10, 2009

(30) Foreign Application Priority Data

Mar. 17, 2006   (GB) .................................. 0605441.5

(51) Int. Cl.
| | | |
|---|---|---|
| A61L 27/56 | (2006.01) | |
| A61L 27/50 | (2006.01) | |
| A61L 27/10 | (2006.01) | |
| A61F 2/28  | (2006.01) | |
| A61F 2/30  | (2006.01) | |

(52) U.S. Cl.
CPC ................. *A61L 27/56* (2013.01); *A61L 27/10* (2013.01); *A61L 27/50* (2013.01); *A61F 2/28* (2013.01); *A61F 2002/30677* (2013.01); *A61F 2310/00293* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,429,691 A  * | 2/1984  | Niwa et al. ...................... 606/77 |
| 4,629,464 A    | 12/1986 | Takata et al. | |
| 5,055,307 A  * | 10/1991 | Tsuru et al. ................... 424/493 |
| 5,204,106 A    | 4/1993  | Schepers et al. | |
| 5,681,872 A  * | 10/1997 | Erbe .............................. 523/114 |
| 6,153,221 A    | 11/2000 | Thut et al. | |
| 6,228,386 B1   | 5/2001  | Yang | |
| 6,692,532 B1   | 2/2004  | Healy et al. | |
| 2005/0233454 A1| 10/2005 | Nies et al. | |

FOREIGN PATENT DOCUMENTS

| | | |
|---|---|---|
| JP | 2004-051408 | 2/2004 |
| WO | 96/00536 A1 | 1/1996 |
| WO | 97/41842 A1 | 11/1997 |
| WO | 98/08773 A1 | 3/1998 |
| WO | 00/20353 A1 | 4/2000 |
| WO | 03/007853 A1 | 1/2003 |

OTHER PUBLICATIONS

PetroWiki, "Gravel pack design", published by SPE International, pp. 1-5: [retrieved on Mar. 9, 2015 from on-line website http://petrowiki.org/Gravel_pack_design].*
Cary A. Shapoff et al., "The Effect of Particle Size on the Osteogenic Activity of Composite Grafts of AHogeneic Freeze-Dried Bone and Autogenous Marrow", J. Periodontol. vol. 51, No. 11, pp. 625-630, 1980.*
International Search Report (date of mailing: Mar. 13, 2008) issued in PCT/GB2007/000960 filed on Mar. 19, 2007 (5 pgs).

* cited by examiner

*Primary Examiner* — Ernst V Arnold
*Assistant Examiner* — Kyung Sook Chang
(74) *Attorney, Agent, or Firm* — Bret E. Field; Makoto Tsunozaki; Bozicevic, Field & Francis LLP

(57) ABSTRACT

A bone replacement filler comprising a biomedical ceramic particulate, wherein the filler is able to flow without the application of an external shear stress or compressive force or under a relatively low shear stress or compressive force, but resists flow or does not flow when subjected to a higher shear stress or compressive force, and wherein at least some of the particles in the ceramic particulate have a micro-porous surface structure and/or a micro-porous sub-surface structure.

16 Claims, No Drawings

BIOMEDICAL FILLER

The present invention relates to biomedical materials and, in particular, to a filler material for bone.

The combined affects of an ageing population and greater expectations in the quality of life have resulted in an increasing global demand for orthopaedic implants for the replacement or augmentation of damaged bones and joints. In the field of bone grafting, current gold standards include the use of autograft and allograft but these methods are increasingly recognised as non-ideal due to morbidity or limitations in supply and consistency. Ceramics have been considered for use as bone graft substitutes to replace or extend traditional bone grafts for over 30 years. In particular, calcium phosphates such as hydroxyapatite have been promoted as a result of their osteoconductive properties.

Accordingly, as surgical technique and medical knowledge continue to advance, there has been a growth in the demand for synthetic bone replacement materials. Consequently, there is an increasing interest in the development of synthetic bone replacement materials for the filling of both load bearing and non-load bearing osseous defects, such as in joint reconstruction, craniomaxillo facial reconstruction, trauma, tumour, vertebral compression fracture and spinal surgery.

WO 03/007853 relates to an expandable porous mesh bag device and its use for bone surgery. The bag is inserted into a prepared cavity in bone and then inflated using bone replacement material to expand and fill the cavity.

Conventional porous ceramic bone grafts often cannot be used in load-bearing applications. In particular, if the biological properties of the material are optimized, then the material generally does not retain sufficient strength to bear physiological loads. This is because ceramic bone grafts must possess both (a) interconnected macroporosity for bone ingrowth and nutrition, and (b) microporous strut porosity to allow protein and cell attachment to the graft prior to repair.

PCT/GB99/03283 describes a method of manufacturing a foamed ceramic material for biomedical applications.

Furthermore, conventional porous ceramic bone grafts are typically either (i) flowable/injectable and non-porous, or (ii) porous and non-injectable/flowable.

The present invention aims to address at least some of the problems associated with the prior art and/or to provide novel biomedical fillers.

Accordingly, the present invention provides a bone replacement filler comprising a biomedical ceramic particulate, wherein the filler is able to flow without the application of an external shear stress or compressive force or under a relatively low shear stress or compressive force, but resists flow or does not flow when subjected to a higher shear stress or compressive force, and wherein at least some of the particles in the ceramic particulate have a micro-porous surface structure and/or a micro-porous sub-surface structure.

Preferably, at least some of the particles in the ceramic particulate have a micro-porous surface structure and a micro-porous bulk structure.

As used herein, by the term macro-porous is meant pores with a modal diameter $d_{mode} \geq \approx 50$ μm, preferably $d_{mode} \geq \approx 100$ μm. By the term micro-porous is meant pores with a modal diameter $0.1\ \mu m \leq d_{mode} \leq 50\ \mu m$, preferably $0.1\ \mu m \leq d_{mode} \leq 40\ \mu m$.

The filler is preferably provided in a substantially dry form, although it may also be provided in the form of a slurry, for example a mixture of the slurry and blood or a blood substitute. The ceramic particulate has a particle size distribution whereby the particulate is able to flow without the application of an external shear stress or compressive force or under a relatively low shear stress or compressive force, but resists flow or does not flow when subjected to a higher shear stress or compressive force.

Such a particulate can be delivered to a site simply by the action of gravity. The use of an external force to facilitate delivery to a site is therefore not essential but merely optional. When delivered to a space or void and subjected to a shearing stress or compressive force, the particles in the particulate come into intimate contact with each other and "lock together" to form a stable, load-bearing filler.

The ceramic particulate may be composed of substantially spherical particles. There is preferably a distribution of particle sizes. This is advantageous because it allows channels and spaces around and between particles through which host bone can grow.

The flowable nature of the filler according to the present invention allows the filler to be simply delivered to the desired site via, for example, a piece of flexible tubing or a cannula.

Advantageously, at least some of the particles of the ceramic particulate comprise at least a micro-porous surface structure. This facilitates surface attachment of proteins and cells, as well as the transmission of nutrients and cytokines. Preferably, the particles also have a microporous bulk structure.

The ceramic particulate preferably has a particle size distribution in which at least 90% of the particles are from 0.04 to 10 mm in equivalent circular diameter, more preferably from 0.05 to 10 mm. Still more preferably, at least 90% of the particles are from 0.05 to 5 mm, even more preferably at least 90% of the particles are from 0.1 to 5 mm in equivalent circular diameter. In a preferred embodiment, at least 90% of the particles are from 0.1 to 2 mm in equivalent circular diameter.

A range of particle sizes of microporous granules may be formed by conventional dry grinding of bulk cast porous ceramic materials such as a calcium phosphate-based materials. The particles may be fractionated by conventional sieving techniques. For example, a sieved mixture of powders may comprise:

40-58 wt % of 40-90 microns
40-58 wt % of 90-125 microns
1-5 wt % of 125-250 microns
1-5 wt % of 250-500 microns More preferably, a sieved mixture of powders may comprise:

42-53 wt % of 40-90 microns
42-53 wt % of 90-125 microns
1-4 wt % of 125-250 microns
1-4 wt % of 250-500 microns Still more preferably, a sieved mixture of powders may comprise:

45-50 wt % of 40-90 microns
45-50 wt % of 90-125 microns
2-3 wt % of 125-250 microns
2-3 wt % of 250-500 microns The ceramic particulate may comprise any of the well known biomedical materials including natural or synthetic bone based on various calcium phosphate materials. Suitable examples include one or more of hydroxyapatite, apatite, substituted-hydroxyapatite (eg silicated calcium-phosphate), substituted-apatite, tricalcium phosphate, alpha or beta polymorphs thereof, calcium silicate, tetracalcium phosphate, calcium carbonate, calcium oxide, monetite, brushite, calcium pyrophosphate and octacalcium phosphate.

These materials are all conventional in the art and there are number of well known processes for their preparation. For example, PCT/GB97/02325 describes a silicate-substituted hydroxyapatite material.

In the present invention, the ceramic particles preferably have interconnected microporosity. When delivered to a space or void and subjected to a shearing stress or compressive force, the particles in the particulate come into intimate contact with each other and "lock together" to form a stable, load-bearing filler. Because the interconnections are between the particles rather than through pores within the particles, advantageous biological properties are maintained while retaining graft strength. In other words, the micro-porous structure of the particles serves as an attachment for proteins and cells, while the spaces between the different sized particles as a macro-pores for bone in-growth. This is to be contrasted with the prior art bone graft materials.

The ceramic particulate according to the present invention is preferably prepared by forming a porous ceramic material. There are a number of well known methods to achieve this such as, for example, as described in PCT/GB99/03283. Preferably, however, the material is made by slip casting a slurry (non-foamed), followed by drying, burn-out of any binder, and then finally sintering and densification. The sintered material can then be comminuted to result in a particulate having microporosity. The desired particle size distribution is achieved by adjustment of the comminuting parameters and/or sieving of the particulate.

In the present invention, the biomedical filler is flowable and also micro and/or macro-porous. Again, this is to be contrasted with the prior art bone graft materials.

Pharmaceutical drugs and/or biologically functional peptides may be infiltrated into the micropores to allow for controlled delivery.

The present invention will now be described further with reference to the following non-limiting examples.

EXAMPLE 1

A range of particle sizes of microporous granules were formed by dry grinding of bulk cast porous silicated calcium-phosphate. The particles were fractionated by sieving and a mixture was formed comprising 47.5 wt % of 40-90 microns, 47.5 wt % of 90-125 microns, 2.5 wt % of 125-250 microns, and 2.5 wt % of 250-500 microns. To this mixture was added 53% by weight blood substitute (63% deionised water and 37% glycerol). The mixture was placed in a peristaltic pump and the pump activated at 20 rpm which delivered the slurry into a model of osteoporotic vertebral cancellous bone (Sawbones Europe AB). Under conditions of low load, the slurry was delivered at a rate of 1.12 g/s. As the local area within the cancellous bone model filled with slurry, the resulting back-pressure generated compressive forces within the mass delivered and within the delivery tube. This caused the slurry to "lock up" and flow ceased.

EXAMPLE 2

A range of particle sizes of microporous granules were formed by dry grinding of bulk cast porous silicated calcium-phosphate. The particles were fractionated by sieving and a particle size range 125-250 microns was reserved. These particles were flowed through a cannula 2.7 mm in diameter under low-stress conditions (gravitational force) into a model of osteoporotic vertebral cancellous bone (Sawbones Europe AB).

The filler according to the present invention finds application in the following medical procedures, which are provided by way of example.

Interbody Fusion

Disc material is removed with care being taken to preserve the remaining anterior/posterior and lateral annulus fibrosis. Once the endplates are exposed, the disc space can be distracted and the filler is then introduced into the disc space. Once filled the distraction force is released. The natural compressive load causes the particulate to lock/bind together to provide a stable, load-bearing filler. The micro-porous structure of the particles serves as an attachment for proteins and cells, while the spaces between the different sized particles act as a macro-pores for bone in-growth.

Pedicle Screw Augmentation

When a screw is removed due to loosening/toggling, a small amount of filler can be delivered down through the pedicle. A screw can then be inserted so as to push aside the particles in the filler and pack them into the spaces created in the bone from the toggling action of the previous, failed screw.

Vertebral Compression Fractures

When a vertebral body has fractured or weakened through metastatic or metabolic disease, an instrument can be put in either through the pedicle or extra-pedicluarly, and a space created. A delivery tube can then be attached and the filler delivered into the space until they come back out of the entrance hole. A small plug can be secured into place to prevent the filler escaping.

The filler according to the present invention may also be used to pack out spaces and improve the implant to bone fixation. For example, in revision knee and hip surgery, the filler may be inserted in between the implant and the bone to provide a filling device to aid primary fixation and secondary stability. This application type is also applicable in trauma surgery for improving screw fixation to increase pull-out strength.

What is claimed is:

1. A bone replacement filler consisting of:
   a biomedical ceramic particulate consisting of a plurality of particles with the following distribution of sizes: 40-58 wt % of 40-90 microns; 40-58 wt % of 90-125 microns; 1-5wt % of 125-250 microns; and 1-5 wt % of 250-500 microns; and
   blood or a blood substitute,
   wherein upon delivery of the filler to a physiological void space and application of a compressive force, the particles in the filler lock together to produce a load-bearing filler that does not flow when subjected to the compressive force.

2. The bone replacement filler as claimed in claim 1, wherein at least some of the particles in the ceramic particulate have a microporous surface structure.

3. The bone replacement filler as claimed in claim 1, wherein the ceramic particulate is composed of substantially spherical particles.

4. The bone replacement filler as claimed in claim 1, wherein the ceramic particulate has a particle size distribution in which at least 90% of the particles are from 0.05 to 10 mm in equivalent circular diameter.

5. The bone replacement filler as claimed in claim 1, wherein the ceramic particulate consists of a plurality of particles with the following distribution of sizes: 42-53 wt % of 40-90 microns; 42-53 wt % of 90-125 microns; 1-4 wt % of 125-250 microns; and 1-4 wt % of 250-500 microns.

6. The bone replacement filler as claimed in claim 5, wherein the ceramic particulate consists of a plurality of particles with the following distribution of sizes: 45-50 wt % of 40-90 microns; 45-50 wt % of 90-125 microns; 2-3 wt % of 125-250 microns; and 2-3 wt % of 250-500 microns.

7. The bone replacement filler as claimed in claim 1, wherein the ceramic particulate comprises one or more of hydroxyapatite, apatite, substituted-hydroxyapatite, substituted-apatite, tricalcium phosphate, alpha or beta polymorphs thereof, calcium silicate, tetracalcium phosphate, calcium carbonate, calcium oxide, monetite, brushite, calcium pyrophosphate and octacalcium phosphate.

8. The bone replacement filler as claimed in claim 2, wherein the particles have interconnected microporosity.

9. The bone replacement filler as claimed in claim 1, wherein at least some of the particles in the ceramic particulate have a microporous sub-surface structure.

10. The bone replacement filler as claimed in claim 2, wherein at least some of the particles in the ceramic particulate have a microporous sub-surface structure.

11. A bone replacement filler consisting of a biomedical ceramic particulate consisting of a plurality of particles with the following distribution of sizes: 40-58 wt % of 40-90 microns; 40-58 wt % of 90-125 microns; 1-5 wt % of 125-250 microns; and 1-5 wt % of 250-500 microns, wherein and upon delivery of the filler to a physiological void space and application of a compressive force, the particles in the filler lock together to produce a load-bearing filler that does not flow when subjected to the compressive force.

12. The bone replacement filler as claimed in claim 1, wherein the filler is provided in the form of a slurry.

13. The bone replacement filler as claimed in claim 1, wherein the filler is present in a pump.

14. The bone replacement filler as claimed in claim 11, wherein at least some of the particles in the ceramic particulate have a microporous surface structure and/or a microporous sub-surface structure.

15. The bone replacement filler as claimed in claim 1, wherein the load-bearing filler is microporous and macroporous.

16. A bone replacement filler consisting of:
a biomedical ceramic particulate consisting of a plurality of particles with the following distribution of sizes: 40-58 wt % of 40-90 microns; 40-58 wt % of 90-125 microns; 1-5 wt % of 125-250 microns; and 1-5 wt % of 250-500 microns, wherein at least some of the particles in the ceramic particulate have a microporous surface structure and/or microporous sub-surface structure; and
one or more pharmaceutical drugs and/or biologically functional peptides infiltrated into the microporous surface structure and/or the microporous sub-surface structure,
wherein upon delivery of the filler to a physiological void space and application of a compressive force, the particles in the filler lock together to produce a load-bearing filler that does not flow when subjected to the compressive force.

* * * * *